United States Patent [19]

Smith

[11] Patent Number: 4,892,524

[45] Date of Patent: Jan. 9, 1990

[54] INTRAVENOUS ADMINISTRATION SYSTEM

[76] Inventor: Gordon Smith, 1320 Pinehill Dr., Jefferson, Tex. 75657

[21] Appl. No.: 115,424

[22] Filed: Oct. 30, 1987

[51] Int. Cl.⁴ .............................................. A61M 5/00
[52] U.S. Cl. .................................... 604/246; 604/245; 604/257
[58] Field of Search ............... 604/246, 245, 254, 256, 604/257, 122, 83

[56] References Cited

U.S. PATENT DOCUMENTS

| | | |
|---|---|---|
| 3,298,367 | 1/1967 | Bergman . |
| 3,690,318 | 9/1972 | Gorsuch . |
| 3,878,869 | 4/1975 | Yamanouchi et al. . |
| 3,931,818 | 1/1976 | Goldowsky . |
| 3,941,126 | 3/1976 | Dietrich et al. . |
| 4,175,558 | 11/1979 | Hess, III et al. . |
| 4,191,183 | 3/1980 | Mendelson . |
| 4,425,123 | 1/1984 | Di Salvo .................... 604/257 X |
| 4,447,230 | 5/1984 | Gula et al. ................. 604/126 X |

*Primary Examiner*—Stephen C. Pellegrino
*Attorney, Agent, or Firm*—Quarles & Brady

[57] ABSTRACT

An apparatus for administering a volumetric flow of parenteral liquids into a patient's system, in which the quantity of liquid flowing into the system may be easily adjusted, is disclosed. The apparatus includes two separate hydrostatic head pressure systems. The first head pressure is from a container, through a metering device with an adjustable fixed orifice to a regulator located a fixed distance below the container. The second head is from the regulator, which is designed to prevent air flow through it, to the patient. Several embodiments of the metering device and of the regulator are disclosed.

16 Claims, 4 Drawing Sheets

INTRAVENOUS ADMINISTRATION SYSTEM

BACKGROUND OF THE INVENTION

1. Field of the Invention

The present invention is generally directed to a liquid administration system and more particularly to an apparatus for administering parenteral liquids from a supply container to a patient, wherein the flow rate is maintained at a constant value without regard to the amount of liquid remaining in the supply container or to changes in pressure exerted on the apparatus.

2. Description of the Prior Art

In the medical practice, it is often necessary to intravenously feed a patient with parenteral liquids, such as blood, plasma, dextrose solutions or the like. Such infusions are customarily carried out by employing intravenous (IV) kits incorporating a supply bottle or other container of liquids suspended above the patient and having a drop counting or drip chamber facilitating the determination of the drip rate therethrough, a drip tube through which the liquid to be infused flows by gravity feed, and an administering needle connected to the drip tube. The infusion rate is controlled in the drip chamber by means of a flow controller such as a pinch clip. When infusions are carried out, the drip tube and needle are initially purged of air, the needle is inserted into a vein, and the flow controller compresses the drip tube to restrict the initial flow of liquid. The number of drops falling through the drip chamber are determined by trial and error adjustment of the flow controller.

A major disadvantage encountered with this type of system is a variation that often takes place in the rate of liquid flow. In this system, a pinch clip is customarily placed under the supply bottle for convenience of operation. As the liquid level in the supply bottle falls, the hydrostatic head pressure providing the driving force for flow through the drip tube decreases. The term "hydrostatic head pressure", as used herein, means the pressure differential resulting from the vertical distance separating the two levels of liquid, in this case the liquid level in the supply container and the liquid level at the point of entry into the patient. Changes in hydrostatic head pressure often result in a substantial fluctuation in the volume of liquid being administered to the patient. The flow rate changes can be caused by situations such as changes in blood pressure, a patient voluntarily or involuntarily raising or lowering his infusion arm, partial clogging of the administering needle and dislodging of the administering needle. If the supply bottle drains itself of liquid, it is also possible to get air into the patient which is a dangerous condition to health. All of these conditions result in a time-consuming depletion of a technician's or nurse's time.

There are many teachings in the art of active complex metering devices intended to provide volumetric, or accurately measured volume per unit time, metering of fluids into the patient. Such active systems are usually complex and costly.

There are a variety of prior art references disclosing systems for administering parenteral liquids. U.S. Pat. No. 3,941,126 to Dietrich, et al. and U.S. Pat. No. 4,191,183 to Mendelson disclose the general concept of multiple intravenous feed lines from multiple supply containers which discharge into a common single chamber and then proceed to the patient. U.S. Pat. No. 3,29S,367 to Bergman discloses an apparatus for administering parenteral liquids, which includes capillary tubes of different sizes to control liquid flow. U.S. Pat. No. 3,690,318 to Gorsuch discloses a metering assembly including multiple orifices of different sizes. U.S. Pat. No. 3,878,869 to Yamanouchi, et al. discloses a liquid transfusion system for transfusing a small quantity of liquid by means of a capillary flow system. U.S. Pat. No. 3,931,818 to Goldowsky discloses a liquid administration apparatus comprising a system for providing a constant flow of liquid by means of a sump and float chamber. U.S. Pat. No. 4,175,558 to Hess, III, et al. discloses a parenteral liquid administering device which includes a backflow regulator valve.

While there are systems disclosed for aiding the constant supply of liquid to a patient, no passive system has been heretofore developed which will simultaneously regulate volumetrically the flow of liquid to the system while maintaining a proper hydrostatic pressure system, thus assuring a precise volumetric flow of a specific quantity of liquid into the patient's body over long time periods without regard to fluctuations in the patient's blood pressure or other situations which may have an effect on the temporary rate of flow of the liquid into the patient's system.

SUMMARY OF THE INVENTION

The present invention is summarized in that an apparatus for delivering fluid to a patient includes two separate hydrostatic systems, the first system of which there may be more than one, includes a fluid container, a metering device with at least one fixed orifice, and tubing to connect to a regulator located a fixed distance below the container. The second system includes the regulator with a shut-off valve to prevent air flow therethrough, and tubing to connect to the patient. The first system delivers a constant volumetric flow fixed by the size of the fixed orifice or orifices and the head between the container and the regulator. The second system delivers the volumetrically measured flow to the patient based on the head pressure of the regulator over the patient, which may vary over time without affecting the volumetric flow of the first system.

The objects of the invention are accomplished by an apparatus for administering a liquid comprising at least one supply container for holding the liquid to be administered, tubing connecting the supply container to an administering needle, and at least two separate hydrostatic systems which, in combination, are designed to establish a steady and unchanging overall flow rate of liquid into the patient. One hydrostatic system, the metering system, is designed to volumetrically regulate the flow and quantity of the liquid from the supply container. The metering system is located downstream of the supply container based on a constant hydrostatic head pressure in the tubing of the metering system. The metering system utilizes a fixed size orifice to combine with the fixed head pressure for delivering a precise amount of the liquid. The second hydrostatic system includes a regulator valve located between the metering system and the administering needle. The regulator valve is positioned a sufficient distance above the patient to provide a second hydrostatic head pressure above the patient to permit flow of the liquid metered into the regulator valve to the patient. The regulator valve is designed to seal off air-tight in the absence of liquid therethrough to prevent air flow to the patient.

From the above, it will be seen that the present invention, which incorporates a dual hydrostatic system for administering parenteral liquids, provides a system for establishing a substantially precise and unchanging liquid flow rate of a determined volume of liquid to a patient.

It is an object of the present invention to provide a fluid flow delivery apparatus that will, over time, deliver a constant volumetric flow of one or more fluids to a patient even if the instantaneous flow of fluid is allowed to vary.

It is another object of the present invention to construct such an apparatus which does not require energy input, other than a hydrostatic head, to operate.

Other objects, advantages and features of the present invention will become apparent from the following specification.

DESCRIPTION OF PREFERRED EMBODIMENTS

In accordance with the present invention, a system for administering parenteral liquids is provided comprising at least one container containing the liquid to be administered, flexible tubing connected to each bottle, and an administering needle through which the liquid flows into the patient by gravity feed. The supply container and flexible tubing are items well-known to the art, examples of which are disclosed in the prior art references discussed previously. The apparatus of the present invention is designed to establish a steady and unchanging overall flow rate of the liquid through the system without regard to changes in the overall pressure of the system such as those changes caused by deviations in the patient's blood pressure or when a patient raises or lowers his arm.

The present invention is characterized by two distinct zones of hydrostatic pressure differential or head. The first zone extends from the fluid container through a metering device to a regulator. The second zone is from the regulator to the patient.

Figure 1:
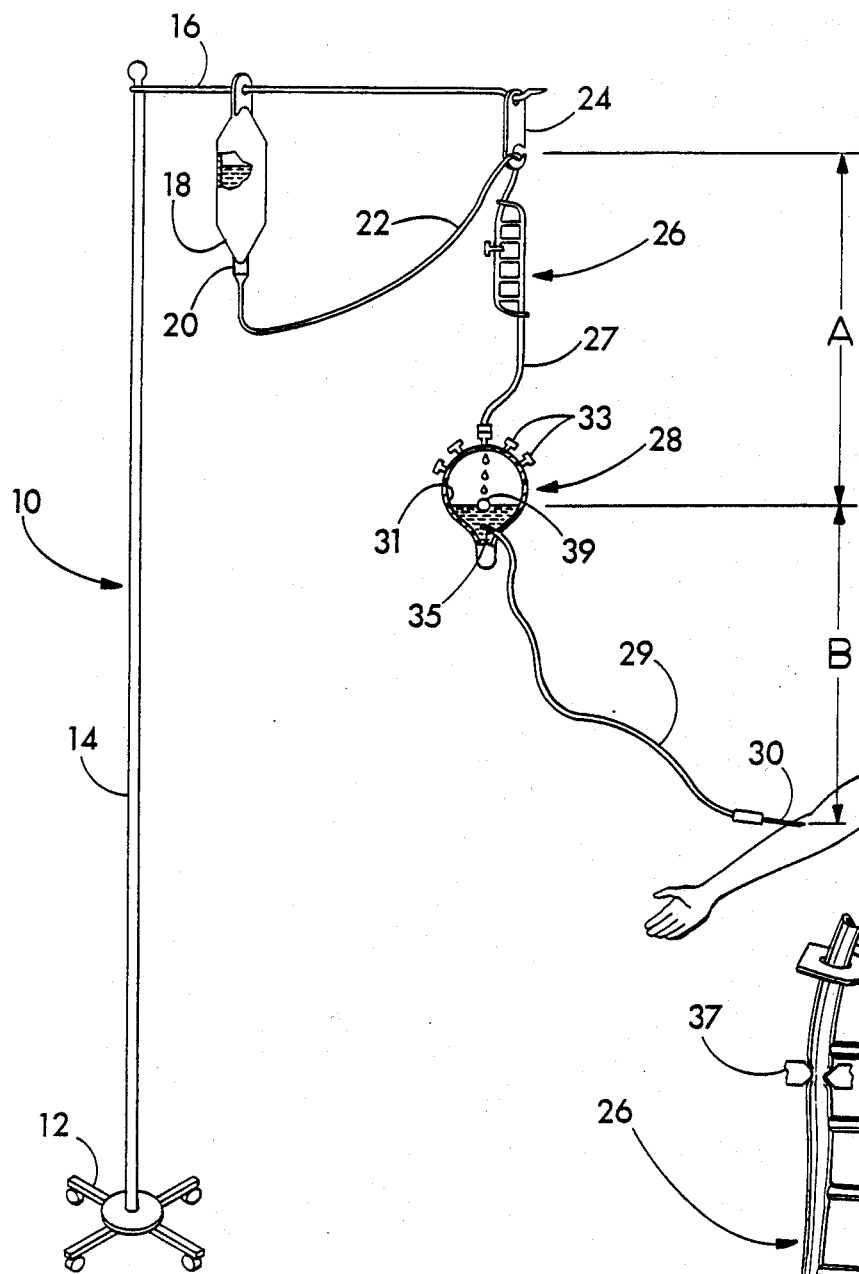
FIG. 1 is a perspective view of an apparatus for administering parenteral liquids of the present invention.

Referring now to the figures in which the same reference numerals will correspond to the same features throughout, a preferred embodiment of the invention, illustrated in FIG. 1, includes a portable supporting structure 10 mounted on wheels or casters 12 upon which a post 14 is attached. The post 14 includes a horizontally disposed arm 16. A supply container 18, typically a flexible plastic bag, and in which plasma, dextrose solution or a like parenteral liquid is contained, is hung on arm 16. The container 18 may include either a separate or an integral drip chamber 20 connected to a first flexible tube 22 made of polyethylene or a like elastomeric material. If desired, the tube 22 may be mounted on arm 16 by a hook 24. At the other end of the drip tube 22 from the supply container 18 is the passive metering device 26. As discussed previously, the metering device 26 should be located a sufficient distance from the supply bottle 18 to effect a substantial hydrostatic head pressure. The metering device 26 serves to provide a mechanism for adjusting very accurately the volume of liquid flowing from the container 18 into the system.

Connected downstream from the metering device 26 is a second tube 27 which connects the output of the metering device 26 to one input to a fluid flow regulator 28. The purpose of the regulator 28 is to allow the flow from more than one container 18 to be joined together and also to ensure that air does not pass into a tube 29 connected below the regulator 28, with the consequent danger that upon refilling of the regulator 28, the weight of the liquid might drive air bubbles through the tube 29 into the patient. As will be described more fully later on in the specification, the regulator 28 is generally a liquid-holding chamber positioned for controlling the flow of the liquid through the tube 29 to the administering needle 30 inserted in the patient. The fully assembled apparatus thus includes both of the metering device 26 and the regulator 28.

If desired, several supply bottles 18, each containing a different medication liquid, may be used in the same kit. The supporting structure 10 will be altered to provide enough arms 16 to hold each supply bottle 18. Each supply bottle 18 will also have connected with it an individual metering device 26 and appropriate tubing. The tubes 27 leaving the metering devices 26 will then all terminate into one regulator 28. The regulator 28 will be augmented by a manifold system which has enough ports to accommodate each of the tubes 27 entering the regulator 28.

Figure 2:
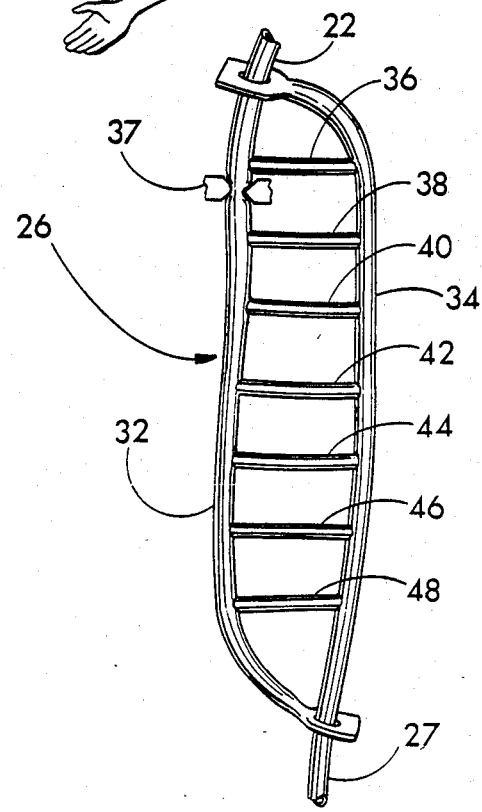
FIG. 2 is an elevated sectional view of one embodiment of the metering system of the present invention.
Figure 3:
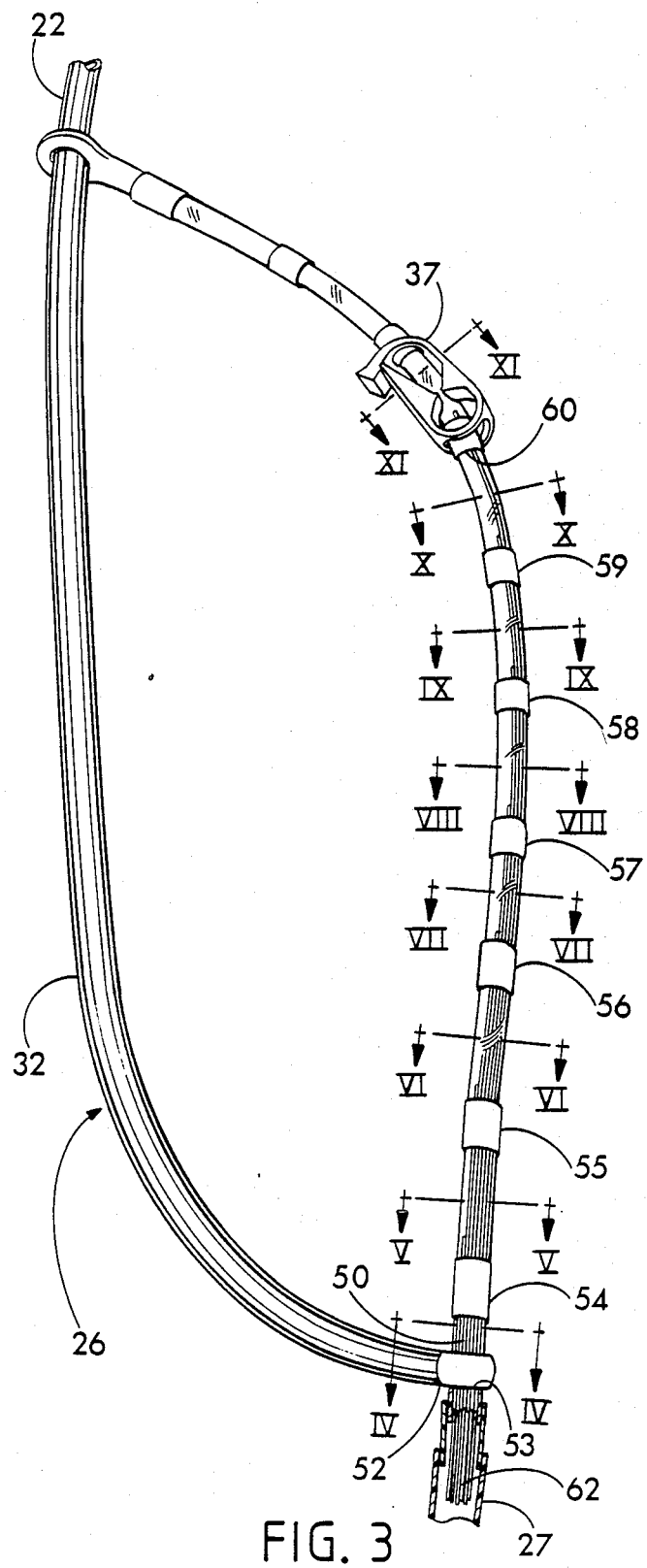
FIG. 3 is an elevated sectional view of another embodiment of the metering system of the present invention.
Figure 11:
FIGS. 4-11 are cross sectional views of the metering system of FIG. 3 taken at lines IV—IV to XI—XI respectively.
Figure 10:
Figure 9:
Figure 8:
Figure 7:

Referring now to FIG. 2, one embodiment of the metering device 26 will be explained. The metering device of FIG. 2 resembles a ladder-like structure comprising a first longitudinal manifold 32 which extends from the tube 22. The first manifold 32 is in fluid communication with a second longitudinal manifold 34 which extends into the drip tube 27. The communication link is through a series of cross-tubes 36, 38, 40, 42, 44, 46, 48 each having an accurately pre-selected and defined internal cross-section. The cross-tubes are thus a series of restricted orifices, each individually much smaller in cross-section than the manifold 32 or tube 22. Although seven cross-tubes 36-48 are illustrated for the purpose of the present invention, it is to be understood that a greater or fewer number of cross tubes can be used as desired. Attached to the first manifold 32 is an adjustable pinch clamp 37, which is known to the art for pinching off the supply of liquid flowing through flexible elastomeric tubing such as that from which the manifold 32 is constructed. It is the location of the pinch clamp 37 which determines the number of cross-tubes which are open and thus the available flow orifices from the supply bottle 18 to the regulator 28. As illustrated in FIG. 2, the pinch clamp 37 may be located in clamping position on first manifold 32 between cross-tubes 36 and 38. In this position, one cross tube 36 is available for liquid communication, as illustrated by the arrows, between the first manifold 32 and the second manifold 34. If the pinch clamp 37 is positioned at a point between the cross-tube 36 and the tube 23, then the entire metering device 26 would be closed off to any liquid flow to the regulator 28. If the adjustable pinch clamp 37 is positioned between cross tubes 38 and 40 on first manifold 32, then two cross tubes 36, 38 are available for liquid communication between first manifold 32 and second manifold 34 thus enabling twice the amount of liquid to flow from the supply bottle 18 to the regulator 28. Thus, by positioning the adjustable pinch clamp 37 on the first manifold 32 between any of cross tubes 36–48, the amount of liquid flowing from the supply bottle 18 to the regulator valve 28 can be adjusted in incremental fixed steps.

The regulator 28, as illustrated in the embodiment of FIG. 1, includes a large chamber 31 into which a plurality of standard IV tubing fittings 33 are connected. A float 39 floats in the liquid in the chamber 31. At the base of the chamber 31 is a small upstanding flexible section of silicone tubing 35 contained in a lower neck portion of the chamber 31 which connects to the tube 29. In its operation, fluid flows into the chamber 31 from any tubing connected to the fittings 33. The float 39 floats on the surface of the fluid level in the chamber 31 and then fluid flows through the silicone tubing 35 and the tube 29 to the patient. If the third level in the chamber 31 falls, the float 39 lowers and pinches the silicone tubing 35 to cut off fluid flow out of the regulator 28. This prevents air from leaving the regulator 28.

In its operation, the fluid administration apparatus of FIG. 1 provides both for volumetric measuring of flow and for completely passive operation. The head, or vertical distance, between the container 18 and the regulator 28 must be accurate at a pre-selected distance (indicated at "A"). This head differential has to be correlated with the size of the restricted orifices in the cross-tubes 36–48 so that at the selected head, a pre-selected accurate volume of flow is produced through each orifice, for example 0.1 ml per second. If this is properly coordinated, then by altering the placement of the pinch clamp 37, it is possible to incrementally and accurately control flow from the container 18 to the regulator 28. Fluid flow from the regulator 28 depends on several variables including the head pressure between the regulator 28 and the patient (indicated at "B"). Thus the rate of fluid flow into the patient over any short time period may vary depending on the movement of the patient, or the patient's blood pressure, or other variables. Since maximum fluid flow out of the regulator 28 should be larger than the average flow into the regulator 28, fluid flow may even cease from time-to-time as the chamber 31 empties. Nevertheless, over long time periods the overall rate of flow from the container 18 to the patient will be fixed and constant because of the fixed and constant nature of the flow into the regulator 28. This is true, and particularly important, if there are two or more containers 18 both connected to the regulator 28 since their relative flow rates will at all times be constant. Thus the apparatus of FIG. 1 functions solely on gravitational energy and yet is still accurate and volumetric in its control of overall flow rate.

An alternative embodiment to the metering device 26 is illustrated in FIGS. 3–11. As with the embodiment of FIG. 2, the metering device 26 of FIG. 3 utilizes first and second manifolds 32, 34. Instead of cross tubes, however, the volume of flow is adjusted by means of interiorly placed tubules 50 made of a silicone or other elastomeric substance known to the art. The tubules 50 serve as the restricted orifices in the metering device 26 of FIG. 3. Attached to the lower end of each of the tubules 50 is a rigid cannula 62, made of stainless steel or other non-toxic substance. The first tube 32 is in fluid connection with the second manifold 34 at a joint designated by reference numeral 52. The liquid flow to the regulator valve 28 is blocked by a plug 53 through which the cannulas 62 extend. Each tubule 50 connects to a cannula 62 in the plug 53 and travels upward through the second manifold 34. The tubules 50 are of varying lengths such that one of each of the tubules 50 ends at a defined location 54, 55, 56, 57, 58, 59, 60. It is within the scope of the present invention to have greater or fewer numbers of tubules 50 as is necessary to fulfill the objects of the present invention.

A pinch clamp 37 is used to pinch off the area of the second manifold 34 between any of locations 54–60. By pinching off any of these locations, only the tubules 50 which end below the pinch clamp 37 will allow liquid flow therethrough. Fluid flows from the manifold 32, through the joint 52, up the manifold 34, through all of the unpinched tubules 50 and associated cannula 62 to the tube 27. For example, if the pinch clamp 48 is placed between location 55 and 56, only two of the tubules 50 will remain open for liquid communication between the supply container 18 and the regulator 28.

Figure 6:
Figure 5:
Figure 4:

The number of tubules 50 which will be pinched off at each location 54–60 are illustrated respectively in FIGS. 4–11. Thus, if the pinch clamp 37 is placed between location 55 and 56; five of the capillary tubes 50 will be pinched off as illustrated in FIG. 6, leaving two of the tubules 50 in liquid communication with the tube 27.

Markings may be positioned on the outside of second manifold 34 at each location 54–60 to indicate the volume of liquid flowing from the capillary tubes to the lumen of second manifold 34 at that point. Thus, if each of the interior tubules 50 has a diameter sufficient to allow 40 mls./hr. of liquid passage, then by pinching off the second manifold 34 between locations 55 and 56, 80 mls. of liquid will pass to the tube 27 each hour. The metering device 26 of FIG. 3 thus, like the metering device of FIG. 2, serves as a selectively restrictable orifice to provide a constant flow therethrough at a fixed hydrostatic pressure.

Figure 12:
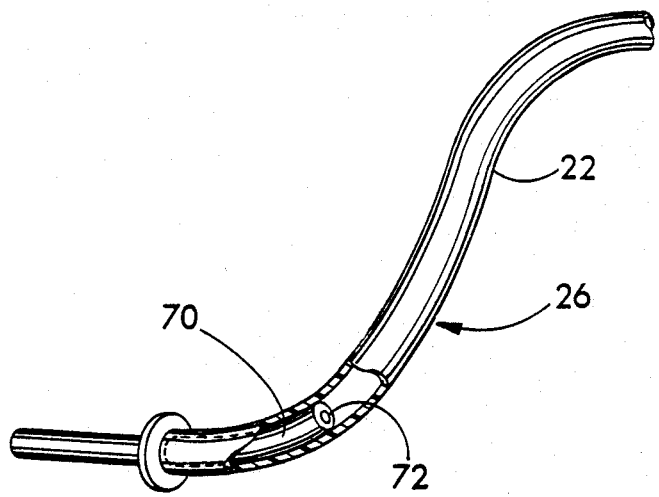
FIG. 12 is an elevated sectional view of a third embodiment of the metering system of the present invention.

In another embodiment, as illustrated in FIG. 12 of the present invention, the metering device 26 is formed of single restricted orifice tube 70 sealingly placed between connector fittings in the tubes 23 and 27. The tube 70 is designed to reduce the interior diameter of the tube, with a restricted passageway 72 extending along its length in order to allow a greatly reduced volume of liquid to pass through the tube 22 to the regulator 28. It is envisioned in this embodiment that the apparatus would be supplied with a series of the tubes 70, each of a different pre-selected size. The different sized tubes 70 may, if convenient, be labeled by size or may be color-coded by size so that the appropriately desired tube 70, with the desired size passageway 72, can be selected and inserted between the tubes 23 and 27.

It is contemplated that the flow resistance cannula 70 can be incorporated with a medicated supply bottle as a unit when being manufactured. The flow is then predetermined to flow as a result of the type of liquid in the supply bottle.

Figure 13:
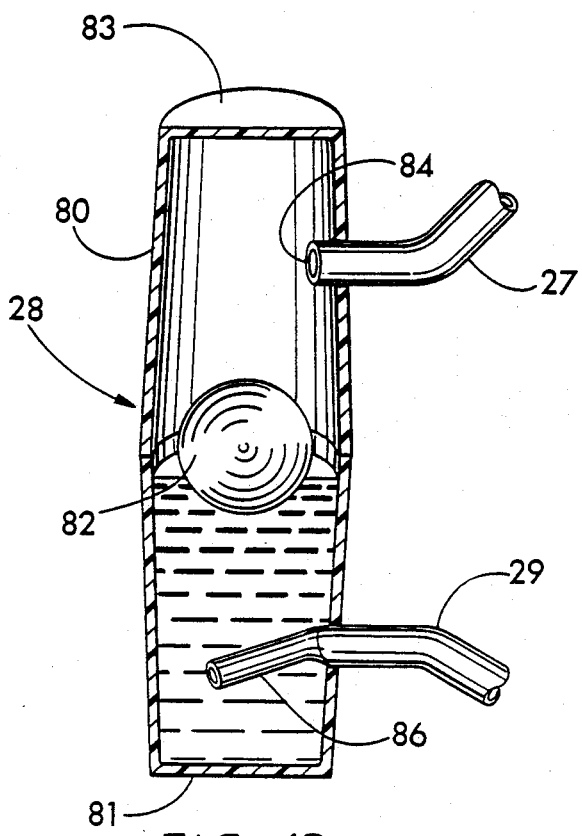
FIG. 13 is a perspective sectional view of one embodiment of the regulator valve of the present invention showing liquid in the system.
Figure 14:
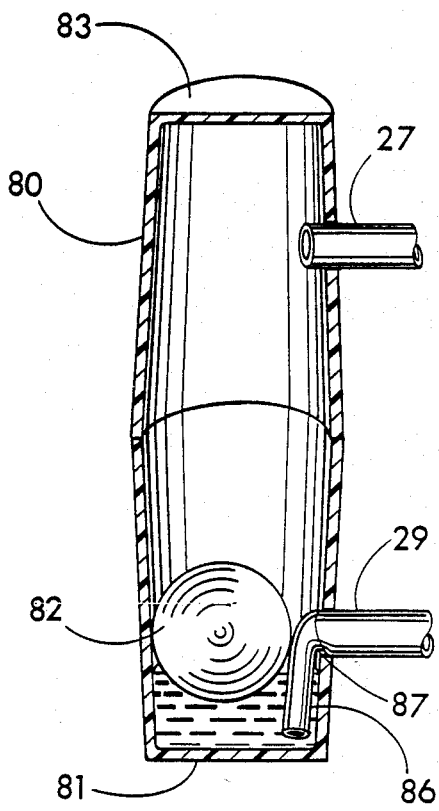
FIG. 14 is a perspective sectional view of the regulator valve of FIG. 13 with the liquid drained from the system.

FIGS. 13 and 14 represent another embodiment of a regulator valve 28. In accordance with this embodiment, the regulator valve 28 includes a chamber 80 in which the interior portion is substantially large enough to house a buoyant ball float 82. As is illustrated in FIGS. 13 and 14, the chamber walls are preferably cylindrical in shape and the float 82 is spherical. The diameter of the float 82 should be greater than one-half but less than the diameter of the cylinder walls of chamber 80. As can be seen in FIG. 13, the tube 27 from the supply bottle 18 enters the side wall of chamber 80 through a fitting 84. There may be additional similar fittings or a third manifold attached to a single fitting to allow multiple containers 18 to be used. The tube 29 which attaches to the regulator valve 28 is attached to a fitting exiting from the lower portion of the cylindrical wall of chamber 80. The drip tube 29 is characterized by a flexible silicone tube extension 86 which is inserted into the interior of chamber 80.

Accordingly, when chamber 80 is at least partially filled with liquid, as illustrated in FIG. 13, the float 82 floats upwardly in the chamber 80. The float 82 is limited in its upward motion by an upper retention member 83 of chamber 80. As the liquid is drained from the chamber 80, the float 82 is allowed to descend to a position adjacent silicone extension 86. As the float 82 rests against the extension 86, it forms a sealing bend 87 in the flexible extension 86, illustrated in FIG. 14, sealing off the tube 29 from the rest of the IV system. Thus, if the liquid has drained from the regulator 28, the regulator will immediately be sealed off protecting the patient from the deleterious effects of air in the blood stream.

Figure 15:
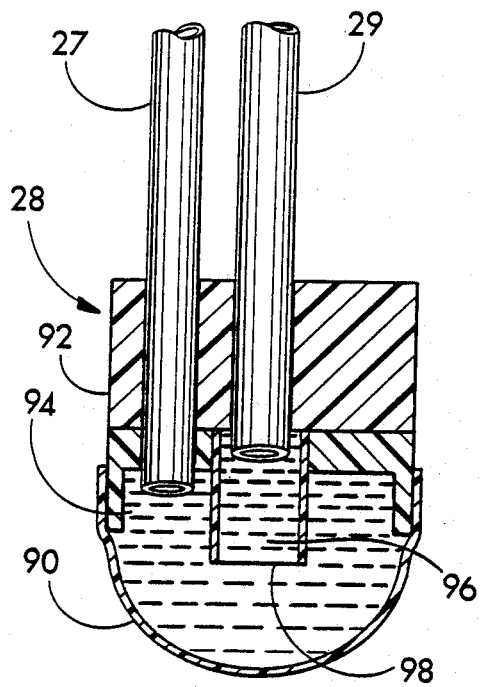
FIG. 15 is an elevated sectional view of another embodiment of the regulator valve of the present invention showing liquid in the system.
Figure 16:
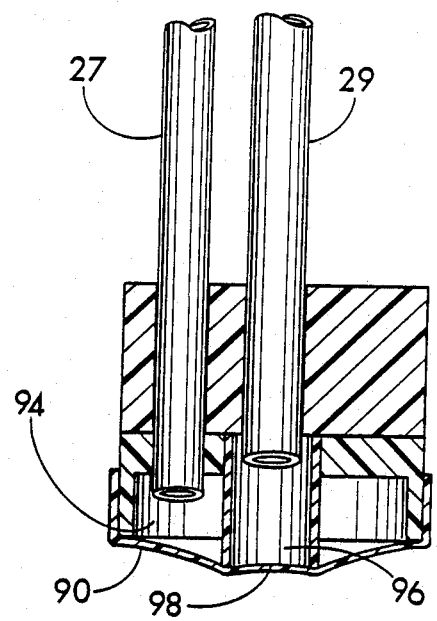
FIG. 16 is an elevated sectional view of the regulator valve of FIG. 15 showing liquid drained from the system.

Another embodiment of the regulator 28 is illustrated with respect to FIGS. 15 and 16 which disclose a flexible molded diaphragm 90, made of silicone or other very flexible substance, in sealing engagement with a rigid base 92. The tubes 27 and 29 are connected by suitable fittings to be in fluid communication with the space created by the sealing relationship of diaphragm 90 and base 92. As illustrated in FIG. 15, the tube 27 ends at a channel 94. On the other hand, the drip tube 29 is surrounded by a cylinder 96. When liquid is present in the regulator, the liquid expands the diaphragm 90, and a constant communication of liquid through the tube 27 is present. However, in the absence of liquid, as illustrated in FIG. 16, the diaphragm 90 reduces in size to form a sealing relationship over the cylinder tube 96.

Figure 17:
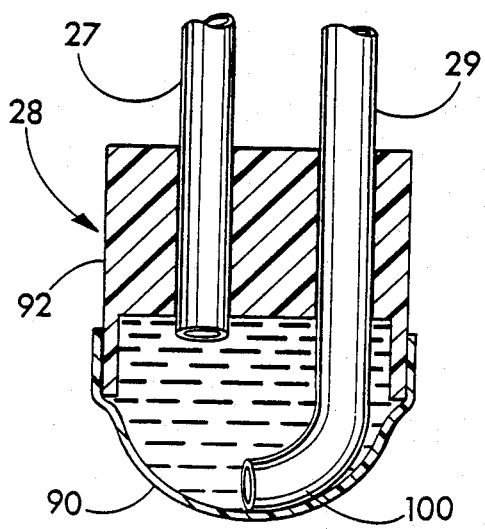
FIG. 17 is an elevated sectional view of a third embodiment of the regulator valve of the present invention showing liquid in the system.
Figure 18:
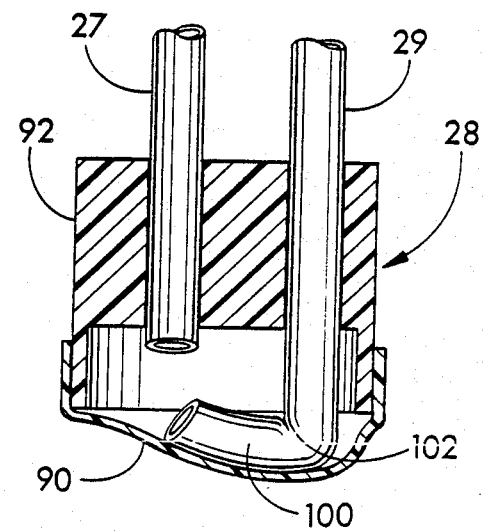
FIG. 18 is an elevated sectional view of the regulator valve of FIG. 17 of the present invention showing liquid drained from the system.

In another embodiment, as illustrated in FIGS. 17 and 18, the cylinder 96 of the previous embodiment is eliminated and a highly flexible silicone tubule 100 connected to the end of the drip tube 29 is added. As illustrated in FIG. 18, in the absence of liquid, diaphragm 90 contracts causing a sealing bend 102 in tubule 100, thus creating a seal in the system.

One of the advantages of this valve regulator system is that when air reaches the valve, it automatically shuts off due to the lack of liquid in the system. Thus, no air can reach the patient. Further, when there is stoppage of liquid flow to the patient, the regulator closes off any flow from the supply bottle.

A preferred method of operation will be discussed using the metering device of FIGS. 3-11 and the regulator of FIGS. 13-14. In operation, the system is first purged of air by means known to the art and administering needle 30 is placed in the patient. The liquid from the supply container 18 is measured into the tube 23 through the chamber 20 according to methods known to the art. The regulator 28 is accurately located a fixed, selected distance from the supply container 18 to create a first hydrostatic head pressure in the system. Generally, a distance of about 18 inches is sufficient. As the liquid from the tube 23 flows into the first manifold 32 of the metering device 26, the liquid will be directed to the interior tubules 50 which are directed upwardly within the second manifold 34. The amount of liquid flowing into the tube 27 will be dependent upon the location of the pinch clamp 37, as previously described. The liquid will flow out of the openings of the interior tubules 50 into the second tube 34 and downwardly through the second manifold 34 to the tubule 27 and ultimately to the regulator 28.

The liquid will flow from the tube 27 into the chamber 80 of the regulator 28 causing the float 82 to rise. The rising of the float 82 in the chamber 80 of the regulator 28 causes the extension 86 of the tube 29 to straighten out, thus eliminating the sealing bend, illustrated at 87 in FIG. 14. By the elimination of the sealing bend 87, a flow communication develops between the liquid flowing from the tube 27 to the tube 29 and ultimately to the administering needle 30 into the patient.

Should a back flow of pressure caused by a sudden fluctuation in the patient's blood pressure or other situations as described previously, occur, the regulator will automatically seal off thus preventing any disruption of liquid entering the patient's system without interfering with the flow metering system. Additionally, if the supply bottle 18 should drain itself, the flow of liquid entering the regulator 28 will be interrupted thus dropping the float 82 towards the lower retention member 81 causing a sealing bend 87 in the extension 86 of the tube 29. This will prevent any possibility of air entering the patient's blood system.

As can be seen from this description, the rate of fluid flow from the container 18 to the regulator 27 will be fixed, and selectable, depending only on the number of open tubules 50 selected by the claim 37. The rate of fluid flow from the regulator 27 into the patient will, of course, vary. The overall average rate of fluid flow into the patient will nevertheless be volumetrically controlled by the metering device 32.

While particular embodiments of this invention have been shown and described, it not intended to limit the same to the details of the construction set forth, but instead, the invention embraces such changes, modifications and equivalents of the various parts in their relationships as come within the scope of the following claims.

What is claimed is:

1. An apparatus for administering a liquid to a patient comprising:
   (a) at least one container for holding liquid suspended elevated above the patient;
   (b) a passive metering device located a sufficient distance from the container to effect a substantial hydrostatic head pressure, the passive metering device containing at least one restricted orifice through which fluid may flow, the metering device located below the container;

(c) a regulator having a fluid chamber and an air-tight exit valve comprising means to obstruct air flow therethrough, the regulator located a pre-selected distance below the container;

(d) first flexible tubing connecting the container to the regulator with the metering device located therebetween so that constant volumetric flow from the container to the regulator is assured by the combination of constant hydrostatic pressure drop from the container to the regulator and the restricted flow through the metering device; and (e) second flexible tubing connecting the output of the regulator to the patient so that instantaneous fluid flow to the patient is determined by the head pressure from the regulator to the patient.

2. The apparatus according to claim 1 wherein the regulator comprises means to receive more than one set of tubing, each tubing being connected to a respective metering device and container.

3. The apparatus according to claim 1 wherein the metering device includes a single lumen tube having an orifice of sufficient diameter to allow a predetermined flow rate of the liquid passing through the metering device.

4. The apparatus according to claim 1 wherein the metering device includes a multi-lumen tube, wherein each of the lumens have successively increasing diameters.

5. The apparatus according to claim 4 wherein the metering device includes an adjustable restriction clamp for adjusting the flow of liquid through the drip tube.

6. The apparatus according to claim 1 wherein the metering device includes: first and second manifolds, the first manifold terminating at a joint in the second manifold; a plug in the second manifold below the joint; a plurality of tubules each incrementally different in length and each positioned in the second manifold extending from a common point, through the plug, past the joint, upward their respective lengths inside of the second manifold, and adjustable means to restrict the second manifold to prevent fluid flow therethrough so that placement of the restriction means allows fluid flow from the first manifold, through the joint into the second manifold, into the tubules not restricted by the restriction means and past the plug, so that the volume of flow through the metering device is controlled by adjustment of the restriction means.

7. The apparatus according to claim 6 wherein the end of each of the plurality of interior tubules extending through the plug includes a rigid tube of similar diameter.

8. The apparatus according to claim 7 wherein the rigid tube is comprised of stainless steel material.

9. The apparatus according to claim 6 wherein the number of non-restricted interior flexible tubules in liquid determines the volume of liquid flowing to the regulator.

10. The apparatus according to claim 1 wherein the regulator includes a chamber in flow communication with the tubing from the metering device, the chamber including:

(a) a base portion positioning the outlets of the tubing to and from the regulator in close proximity with each other, wherein the outlets of the tubing extend from one end of the base portion, the base portion further including a tubular structure surrounding and having an end extending beyond the outlet of the tubing out of the regulator; and (b) a flexible diaphragm in sealing relationship with the base portion and surrounding the tubing outlets, the flexible diaphragm expanding in the presence of liquid to allow liquid communication through the regulator and wherein the diaphragm forms a sealing relationship with the tubular structure end in the absence of liquid.

11. The apparatus according claim 1 wherein the regulator comprises a chamber in flow communication with the tubing into and out of it, the chamber comprising:

(a) a base portion positioning the outlets of the tubing in close proximity, wherein the outlets of the two tubing extend from one end of the base portion, wherein the outlet of one of the tubing is comprised of a flexible extension tube extending from the base portion; and (b) a flexible diaphragm in sealing relationship with the base portion and surrounding the tubing outlets, the flexible diaphragm expanding in the presence of liquid to allow liquid communication between the outlets, wherein the flexible diaphragm positions against the flexible extension in such a manner as to form a sealing bend in the flexible extension in the absence of liquid.

12. An apparatus for administering a liquid to a patient comprising:

(a) at least one container for holding liquid suspended elevated above the patient;

(b) a passive metering device containing at least one restricted orifice through which fluid may flow, the metering device located below the container wherein the metering device is defined by at least two cross-tubes of a defined lumen diameter communicating a first manifold with a second manifold, wherein the cross-tubes are in spaced relationship from each other, the metering device further including an adjustable means for restricting one of the manifolds whereby the location of the restriction means determines the number of connection tubes in liquid communication between the first and second manifolds and thus determines the volume of liquid passing through the metering device;

(c) a regulator having a fluid chamber and an air-tight exit valve comprising means to obstruct air flow therethrough, the regulator located a pre-selected distance below the container;

(d) first flexible tubing connecting the container to the regulator with the metering device located therebetween so that constant volumetric flow from the container to the regulator is assured by the combination of constant hydrostatic pressure drop from the container to the regulator and the restricted flow through the metering device; and (e) second flexible tubing connecting the output of the regulator to the patient so that instantaneous fluid flow to the patient is determined by the head pressure from the regulator to the patient.

13. The apparatus according to claim 12 wherein the metering device, the first and second manifolds and the cross-tubes are comprised of a flexible tubular material.

14. An apparatus for administering a liquid to a patient comprising:

(a) at least one container for holding liquid suspended elevated above the patient;

(b) a passive metering device containing at least one restricted orifice through which fluid may flow, the metering device located below the container;

(c) a regulator having a fluid chamber and an air-tight exit valve comprising means to obstruct air flow therethrough, the regulator located a pre-selected distance below the container, wherein the regulator comprises:

a liquid holding chamber in flow communication with the tubing from the metering device, wherein a flexible extension of the tubing to the patient extends into the chamber;

a buoyant float ball within the chamber, wherein the chamber has apertured retention means surrounding the float ball and proportioned to permit the float ball to float in spaced relation in the presence of liquid passing through the apertured retention means;

wherein the ball is positioned against the extension in the absence of sufficient liquid to float the ball, the positioning effecting a sealing bend in the extension;

(d) first flexible tubing connecting the container to the regulator with the metering device located therebetween so that constant volumetric flow from the container to the regulator is assured by the combination of constant hydrostatic pressure drop from the container to the regulator and the restricted flow through the metering device; and (e) second flexible tubing connecting the output of the regulator to the patient so that instantaneous fluid flow to the patient is determined by the head pressure from the regulator to the patient.

15. The apparatus according to claim 14 wherein the chamber is generally cylindrical in shape.

16. In an apparatus for administering a parenteral liquid from a supply container to a patient wherein the apparatus includes tubing extending from a supply container to the patient, the improvement comprising a regulator located on the tubing between a first portion of the tubing extending from the supply container and a second portion of the tubing extending to the patient, the regulator comprising a liquid holding chamber in flow communication with the first and second portions of the tubing, wherein a flexible extension of the second portion of the tubing extends into the chamber, a buoyant float ball within the chamber wherein the chamber has appertured retention means surrounding the float ball and proportioned to permit the float ball to float in spaced relation in the presence of liquid passing through the appertured retention means.

wherein the ball is positioned against the flexible extension in the absence of sufficient liquid to float the ball, the positioning effecting a sealing bend in the flexible extension.

* * * * *